(12) United States Patent
Panattoni

(10) Patent No.: US 6,846,881 B2
(45) Date of Patent: Jan. 25, 2005

(54) PREPARATION OF DEFECT-FREE POLYACRYLAMIDE ELECTROPHORESIS GELS IN PLASTIC CASSETTES

(75) Inventor: Cory M. Panattoni, Winters, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 10/087,140

(22) Filed: Feb. 27, 2002

(65) Prior Publication Data

US 2003/0162891 A1 Aug. 28, 2003

(51) Int. Cl.[7] ............................. C08F 4/00; C08F 120/56
(52) U.S. Cl. .................... 525/329.4; 524/916; 526/234; 526/934
(58) Field of Search ................................. 526/234, 934; 524/916; 525/329.4; 204/470

(56) References Cited

U.S. PATENT DOCUMENTS 3,755,280 A * 8/1973 Saunders
4,806,434 A * 2/1989 Ogawa
4,940,763 A * 7/1990 Flesher et al.
5,292,665 A * 3/1994 Hochstrasser et al.
5,753,095 A * 5/1998 Alpenfels et al.
6,110,340 A * 8/2000 Lau et al.

OTHER PUBLICATIONS

Andrews, Electrophoresis—Theory, Techniques and Biochemical and Clinical Applications, 2d Ed., Oxford Science Publications (1986), pp. 87–88.
Hames and Rickwood, Gel Electrophoresis of Proteins—a Practical Approach, 2d Ed., Oxford University Press (199)), pp. 32–38.

* cited by examiner

*Primary Examiner*—Tae H. Yoon
(74) *Attorney, Agent, or Firm*—Townsend and Townsend and Crew LLP

(57) ABSTRACT

Irregularities in the pore structures of polyacrylamide gels that are formed in cassettes against plastic walls are reduced or eliminated by the inclusion of an oxygen scavenger in the gel-forming solution. Avoidance of the irregularities results in electropherograms with fewer distortions in the solute bands.

13 Claims, No Drawings

PREPARATION OF DEFECT-FREE POLYACRYLAMIDE ELECTROPHORESIS GELS IN PLASTIC CASSETTES

BACKGROUND OF THE INVENTION

1. Field of the Invention

This invention relates to polyacrylamide gels as used in slab gel electrophoresis.

2. Description of the Prior Art

Slab gels are particularly useful for electrophoresis in view of their ability to accommodate multiple sample analyses and the ease with which the electropherograms can be observed and read by simply identifying the locations of the various bands on the gels that correspond to the individual components. Polyacrylamide is a gel material that is widely used in slab gels.

Slab gels are frequently supplied in pre-cast form, retained between two flat transparent plates in a cassette. The plates are typically made of plastic, and a difficulty that has been observed is an apparent distortion of the solute bands due to irregularities in the gel pore size near the interface between the gel and the plastic. These irregularities are detrimental to the electrophoretic analysis since the pore size affects the migration of the solute bands, and pore size variations cause distortions of the bands.

Polyacrylamide gels are formed from acrylamide monomers and bis-acrylamide crosslinkers by free radical reactions, and molecular oxygen is known to inhibit free radical formation and thereby to limit the growth of the polyacrylamide chain. The problem is particularly acute with polyacrylamide gels formed in plastic enclosures.

SUMMARY OF THE INVENTION

The present invention resides in the discovery that the interface irregularities of polyacrylamide gels that are pre-cast in plastic gel cassettes can be reduced or eliminated by the inclusion of an oxygen scavenger in the gel-forming solution from which the gel is cast. The monomer mixture in the solution is polymerized with the scavenger present in the solution, and the result is a pre-cast gel with a substantially uniform pore size throughout. Band resolution in the cassette is then comparable to the band resolution that can be obtained with polyacrylamide gels in glass enclosures.

Further details of the invention and its preferred embodiments are set forth below.

DETAILED DESCRIPTION OF THE INVENTION AND PREFERRED EMBODIMENTS

Oxygen scavengers that can be used in the practice of this invention include many of the materials that have been used or disclosed for use as oxygen scavengers in such applications as boiler operations where they are included for purposes of reducing corrosion. Examples of these materials are sodium sulfite, sodium bisulfite, sodium thiosulfate, sodium lignosulfate, ammonium bisulfite, hydroquinone, diethylhydroxyethanol, diethylhydroxylamine, methylethylketoxime, ascorbic acid, erythorbic acid, and sodium erythorbate. Oxygen scavengers of particular interest in the present application are sodium sulfite, sodium bisulfite, sodium thiosulfate, sodium lignosulfate, and ammonium bisulfite, and of these, sodium sulfite and sodium bisulfite are the most preferred.

The gel-forming solution is an aqueous solution of a monomer mixture that is polymerizable, generally by a free-radical reaction, to form polyacrylamide. Monomer mixtures that have been used or are disclosed in the literature for use in forming polyacrylamide gels can be used in the practice of this invention. The monomer mixture typically includes acrylamide, a crosslinking agent, and a free radical initiator. Preferred crosslinking agents are bisacrylamides, and a particularly convenient crosslinking agent is N,N'-methylene-bisacrylamide.

The gel-forming solution will also typically include a free radical initiator system. The most common system used is N,N,N',N'-tetramethylenediamine (TEMED) in combination with ammonium persulfate. Other systems will be apparent to those skilled in the art.

Among those skilled in the use of electrophoresis and the preparation of electrophoresis gels, polyacrylamide gels are characterized by the parameters T and C, which are expressed as percents and defined as follows (in which "bis" denotes the bisacrylamide crosslinker):

$$T = \frac{\text{(combined weight of acrylamide and bis in grams)}}{\text{(volume of aqueous solution in mL)}} \times 100$$

$$C = \frac{\text{(weight of bis)}}{\text{(combined weight of acrylamide and bis)}} \times 100$$

The values of T and C can vary in the present invention as they do in the use of polyacrylamide gels in general. For the purposes of the present invention, a preferred range of T values is from about 5% to about 30%, and most preferably from about 10% to about 20%. A preferred range of C values of from about 1% to about 10% (corresponding to a range of weight ratio of acrylamide to bisacrylamide of from about 10:1 to about 100:1), and most preferably from about 2% to about 4% (corresponding to a range of weight ratio of acrylamide to bisacrylamide of from about 25:1 to about 50:1).

The plastic materials used to form the support plates of the cassettes that will benefit from this invention include a wide variety of plastics. The plastics are generally injection moldable plastics, and the selection is limited only by the need for the plastic to be inert to the gel-forming solution, the gel itself, the solutes (typically proteins) in the samples to be analyzed in the cassette, the buffering agents, and any other components that are typically present in the samples. Examples of these plastics are polycarbonate, polystyrene, acrylic polymers, styrene-acrylonitrile copolymer (SAN, NAS), BAREX® acrylonitrile polymers (Barex Resins, Naperville, Ill., USA), polyethylene terephthalate (PET), polyethylene terephthalate glycolate (PETG), and poly (ethylene naphthalenedicarboxylate) (PEN).

The amount of oxygen scavenger included in the gel-forming solution is not critical to the invention and can be varied over a wide range. Certain plastics will require a greater amount of oxygen scavenger than others since the amount of oxygen retained in the plastic varies among different plastics and the manner in which they are formed. The optimal amount of oxygen scavenger may also vary with the choice of scavenger. In general, however, best results will be obtained with a concentration of oxygen scavenger that is within the range of from about 1 mM to about 30 mM, and preferably from about 3 mM to about 15 mM, in the aqueous gel-forming solution. The amount of oxygen scavenger used may also affect the optimal amounts of the other components. For example, certain oxygen scavengers display catalytic activity toward the free radical reaction, and a lower concentration of free radical initiator can then be used when such scavengers are present. When a sulfite or bisulfite is used, for example, the concentrations of TEMED and ammonium persulfate (or other free radical initiator system) can be lower than would otherwise be used.

The following examples are offered for illustrative purposes and is not intended to limit the scope of the invention.

EXAMPLE 1

A gel-forming solution was prepared by combining the following components in an aqueous solution in the concentrations indicated:

acrylamide/N,N'-methylene-bisacrylamide (T=12%, C=2.67%)

0.375 M tris—HCl (tris(hydroxymethyl)aminomethane hydrochloride), pH 8.6

0.067% TEMED 0.05% ammonium persulfate 6 mM sodium sulfite

The acrylamide/bisacrylamide mixture in the solution was allowed to polymerize at room temperature (approximately 20° C.) for 30–60 minutes to form a gel ready for electrophoresis.

EXAMPLE 2

The following solutions were prepared for use in forming resolving and stacking gels for a gel cassette constructed with one glass plate and one acrylic plastic plate. All percents are by weight unless otherwise indicated, and all solutions are aqueous solutions.

TABLE I

| Resolving Gel: | deionized H$_2$O | 34.5 mL |
|---|---|---|
| | 1.5 M Tris-HCl, pH 8.8 | 25.0 mL |
| | 30% (37.5:1) acrylamide/bisacrylamide | 40.0 mL |
| | 10% ammonium persulfate | 500 µL |
| | TEMED | 50 µL |
| Stacking Gel: | deionized H$_2$O | 6.2 mL |
| | 1.5 M Tris-HCl, pH 6.8 | 2.5 mL |
| | 30% (37.5:1) acrylamide/bisacrylamide | 1.3 mL |
| | 10% ammonium persulfate | 50 µL |
| | TEMED | 10 µL |

A stock solution of sodium sulfite (1 M aqueous) was also prepared, and added to the resolving and stacking gel solutions in different levels as follows:

(1) No sodium sulfite added to either gel (2) 57.1 µL of stock solution added to both gel solutions to a final sodium sulfite concentration of 72.02 µg/mL (0.571 mM) in each solution (3) 571.4 µL of stock solution added to both gel solutions to a final sodium sulfite concentration of 720.2 µg/mL (5.714 mM) in each solution The gel solutions were placed in the cassette described above, in a gel space measuring 7 cm×8.3 cm×1 mm. The gels were allowed to polymerize and were then loaded with an E. coli lysate in some bands and a standard protein mixture in others. The standard protein mixture was myosin (200 kD), β-galactosidase (116 kD), phosphorylase B (97.4 kD), bovine serum albumin (66.2 kD), ovalbumin (45 kD), carbonic anhydrase (31 kD), trypsin inhibitor (21.5 kD), and lysozyme (14.5 kD). Upon electrophoresis (SDS-PAGE), distortion of the solute bands (i.e., curving upward toward the outer edges) appeared in the end lanes of the standard protein mixture in all gels but was most pronounced in the gels without sodium sulfite and with only 0.571 mM sodium sulfite. In addition, the bands from both the E. coli lysate and the standard protein mixture were less broad and sharper with the 5.714 mM sodium sulfite.

EXAMPLE 3

The following solutions were prepared for use as resolving and stacking gels for a gel cassette formed from two plates of uncoated polystyrene-acrylonitrile copolymer (SAN 880B TYRIL®, The Dow Chemical Company, Midland, Mich., USA). All percents are by weight unless otherwise indicated, and all solutions are aqueous solutions.

TABLE II

| Resolving Gel: | deionized H$_2$O | 34.5 mL |
|---|---|---|
| | 1.5 M Tris-HCl, pH 8.8 | 25.0 mL |
| | 30% (37.5:1) acrylamide/bisacrylamide | 40.0 mL |
| | 10% ammonium persulfate | 500 µL |
| | TEMED | 50 µL |
| Stacking Gel: | deionized H$_2$O | 6.2 mL |
| | 1.5 M Tris-HCl, pH 6.8 | 2.5 mL |
| | 30% (37.5:1) acrylamide/bisacrylamide | 1.3 mL |
| | 10% ammonium persulfate | 50 µL |
| | TEMED | 10 µL |

A stock solution of 1 M aqueous sodium sulfite was also prepared and added to the resolving and stacking gel solutions in different levels as follows:

(1) No sodium sulfite added to either gel (2) 57.1 µL of stock solution added to both gel solutions to a final sodium sulfite concentration of 72.02 µg/mL (0.571 mM) in each solution (3) 571.4 µL of stock solution added to both gel solutions to a final sodium sulfite concentration of 720.2 µg/mL (5.714 mM) in each solution The gel solutions were placed in the all-plastic cassette indicated above, in a gel space measuring 7 cm×8.3 cm×1 mm. The gels were allowed to polymerize and were then loaded with the same protein mixtures used in Example 2, in different lanes of the gel. Upon electrophoresis (SDS-PAGE), distortion of the solute bands (i.e., wavy bands) appeared in all lanes of the gels without sodium sulfite and with only 0.571 mM sodium sulfite, while the solute bands in the gel containing 5.714 mM sodium sulfite were noticeably straighter. In addition, the bands with the 5.714 mM sodium sulfite were less broad and sharper.

The foregoing description is primarily for purposes of illustration. Further modifications, substitutions and variations will be apparent to those skilled in the art and will be included within the scope of the invention.

What is claimed is:

1. A method for casting a polyacrylamide gel in a plastic gel enclosure, said method comprising (a) forming an aqueous solution of a monomer mixture comprising acrylamide, a crosslinking agent, and an oxygen scavenger which is a member selected from the group consisting of sodium sulfite, sodium bisulfite, sodium thiosulfate, sodium lignosulfate, ammonium bisulfite, hydroquinone, diethylhydroxyethanol, diethylhydroxylamine, methylethylketoxime, ascorbic acid, erythorbic acid, and sodium erythorbate; and (b) polymerizing said monomer mixture in an uncoated plastic gel enclosure to form a polyacrylamide gel.

2. A method in accordance with claim 1 in which said monomer mixture further comprises a free radical initiator.

3. A method in accordance with claim 1 in which said oxygen scavenger is a member selected from the group consisting of sodium sulfite, sodium bisulfite, sodium thiosulfate, sodium lignosulfate, and ammonium bisulfite.

4. A method in accordance with claim 1 in which said oxygen scavenger is a member selected from the group consisting of sodium sulfite and sodium bisulfite.

5. A method in accordance with claim 1 in which said oxygen scavenger is sodium sulfite.

6. A method in accordance with claim 1 in which the concentration of said oxygen scavenger in said aqueous solution is from about 1 mM to about 30 mM.

7. A method in accordance with claim 3 in which the concentration of said oxygen scavenger in said aqueous solution is from about 1 mM to about 30 mM.

8. A method in accordance with claim 3 in which the concentration of said oxygen scavenger in said aqueous solution is from about 3 mM to about 15 mM.

9. A method in accordance with claim 1 in which said plastic gel enclosure is a member selected from the group consisting of polycarbonate, polystyrene, styrene-acrylonitrile copolymer, polyethylene terephthalate, polyethylene terephthalate glycolate, and poly(ethylene naphthalenedicarboxylate).

10. A method in accordance with claim 1 in which said monomer mixture comprises acrylamide and N,N'-methylene-bisacrylamide in aqueous solution, the total of said acrylamide and N,N'-methylene-bisacrylamide amounting to from about 5 to about 30% of said aqueous solution.

11. A method in accordance with claim 1 in which said monomer mixture comprises acrylamide and N,N'-methylene-bisacrylamide at a combined concentration of from about 10 to about 20% of said aqueous solution.

12. A method in accordance with claim 10, in which the weight ratio of acrylamide to N,N'-methylene-bisacrylamide is from about 10:1 to about 100:1.

13. A method in accordance with claim 10 in which the weight ratio of acrylamide to N,N'-methylene-bisacrylamide is from about 25:1 to about 50:1.

* * * * *